United States Patent
Maur et al.

(10) Patent No.: US 12,251,255 B2
(45) Date of Patent: Mar. 18, 2025

(54) INTRA-ORAL BITE DEVICE AND METHOD OF RECORDING AN ANATOMICAL FEATURE OF A PATIENT BY USING THE INTRA-ORAL BITE DEVICE

(71) Applicant: DENTSPLY SIRONA Inc., York, PA (US)

(72) Inventors: Susanne Maur, Bensheim (DE); Markus Hülsbusch, Bensheim (DE)

(73) Assignee: Dentsply Sirona Inc., York, PA (US)

( * ) Notice: Subject to any disclaimer, the term of this patent is extended or adjusted under 35 U.S.C. 154(b) by 365 days.

(21) Appl. No.: 17/619,424

(22) PCT Filed: Jun. 18, 2020

(86) PCT No.: PCT/EP2020/066921
§ 371 (c)(1),
(2) Date: Dec. 15, 2021

(87) PCT Pub. No.: WO2020/260122
PCT Pub. Date: Dec. 30, 2020

(65) Prior Publication Data
US 2022/0240884 A1    Aug. 4, 2022

(30) Foreign Application Priority Data
Jun. 27, 2019   (EP) ..................... 19182891

(51) Int. Cl.
*A61B 6/51*    (2024.01)
*A61B 6/00*    (2006.01)
(Continued)

(52) U.S. Cl.
CPC .............. *A61B 6/542* (2013.01); *A61B 6/461* (2013.01); *A61B 6/469* (2013.01); *A61B 6/512* (2024.01);
(Continued)

(58) Field of Classification Search
CPC ......... A61B 6/542; A61B 6/461; A61B 6/512; A61B 6/51; A61B 5/0053; A61B 5/0088;
(Continued)

(56) References Cited

U.S. PATENT DOCUMENTS

2006/0056582 A1   3/2006  Stoeckl
2008/0299511 A1*  12/2008 Thoms ................ A61B 6/04
                                                    433/68
(Continued)

FOREIGN PATENT DOCUMENTS

CN   102507052 A   6/2012
CN   105496430 A   4/2016
(Continued)

OTHER PUBLICATIONS

International Search Report; PCT/EP2020/066921; Sep. 29, 2020 (completed); Oct. 8, 2020 (mailed).
(Continued)

*Primary Examiner* — Dani Fox
*Assistant Examiner* — Mamadou Faye
(74) *Attorney, Agent, or Firm* — SCHWEGMAN LUNDBERG & WOESSNER, P.A.

(57) ABSTRACT

The present invention relates to an intra-oral bite device for use with an x-ray recording apparatus for recording the image of at least one oral area of a patient, located by the intra-oral bite device.

4 Claims, 3 Drawing Sheets

(51) Int. Cl.
*A61B 6/46* (2024.01)
*A61C 9/00* (2006.01)

(52) U.S. Cl.
CPC .......... *A61C 9/0006* (2013.01); *A61C 9/0046* (2013.01); *A61C 2201/007* (2013.01)

(58) Field of Classification Search
CPC ..... A61B 5/4547; A61B 5/0064; A61B 5/228; A61B 90/16; A61C 9/0006; A61C 9/0046; A61C 2201/007; A61C 9/0053
See application file for complete search history.

(56) References Cited

U.S. PATENT DOCUMENTS

| 2009/0323891 | A1 | 12/2009 | Borghese | |
|---|---|---|---|---|
| 2015/0237958 | A1* | 8/2015 | Cross | A43B 13/02 36/103 |
| 2015/0305669 | A1 | 10/2015 | Hultgren | |
| 2015/0327958 | A1 | 11/2015 | Llop | |
| 2021/0307705 | A1* | 10/2021 | Kim | A61B 6/487 |

FOREIGN PATENT DOCUMENTS

| DE | 102015211166 | A1 | 12/2016 |
|---|---|---|---|
| EP | 1560520 | A1 | 8/2005 |
| EP | 1793739 | A1 | 6/2007 |
| EP | 3756617 | | 12/2020 |
| JP | 2006320347 | A | 11/2006 |
| JP | 2008510535 | A | 4/2008 |
| KR | 20120069846 | A | 6/2012 |
| KR | 1020180033106 | A | 4/2018 |
| WO | 2004039261 | A1 | 5/2004 |
| WO | 2006024342 | A1 | 3/2006 |
| WO | 2011076416 | A1 | 6/2011 |
| WO | 20110120622 | A1 | 10/2011 |
| WO | 2020260122 | | 12/2020 |

OTHER PUBLICATIONS

International Preliminary Report on Patentability; PCT/EP2020/066921; Sep. 29, 2020 (completed); Oct. 8, 2020 (mailed).
Written Opinion of the International Searching Authority; PCT/EP2020/066921; Sep. 29, 2020 (completed); Oct. 8, 2020 (mailed).
"European Application Serial No. 19182891.2, Extended European Search Report mailed Apr. 9, 2019", 11 pgs.
"European Application Serial No. 19182891.2, Response filed May 18, 2021 to Extended European Search Report mailed Apr. 9, 2019", 53 pgs.
"European Application Serial No. 19182891.2, Communication Pursuant to Article 94(3) EPC mailed Feb. 22, 2023", 5 pgs.
"European Application Serial No. 19182891.2, Response filed Jun. 11, 2023 to Communication Pursuant to Article 94(3) EPC mailed Feb. 22, 2023", 57 pgs.
"European Application Serial No. 19182891.2, Communication Pursuant to Article 94(3) EPC mailed Jul. 26, 2023", 5 pgs.
"European Application Serial No. 19182891.2, Response filed Nov. 27, 2023 to Communication Pursuant to Article 94(3) EPC mailed Jul. 26, 2023", 54 pgs.
Logozzo, Silvia, "A Comparative Analysis of Intraoral 3d Digital Scanners for Restorative Dentistry", The Internet Journal of Medical Technology, ISSN: 1559-4610, vol. 5, No. 1, (2011), 1-18.
Japanese Office Action dated May 28, 2024.

* cited by examiner

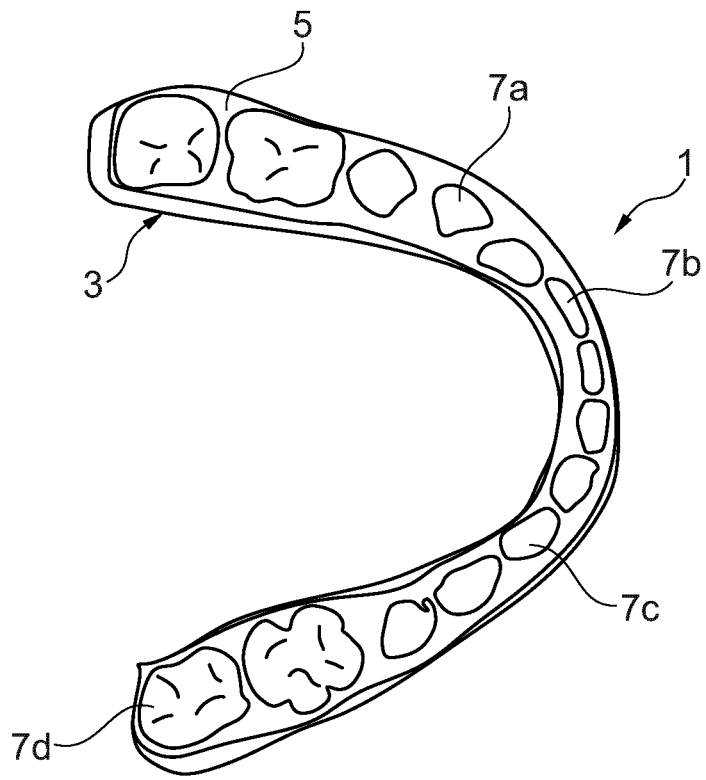
Fig. 1
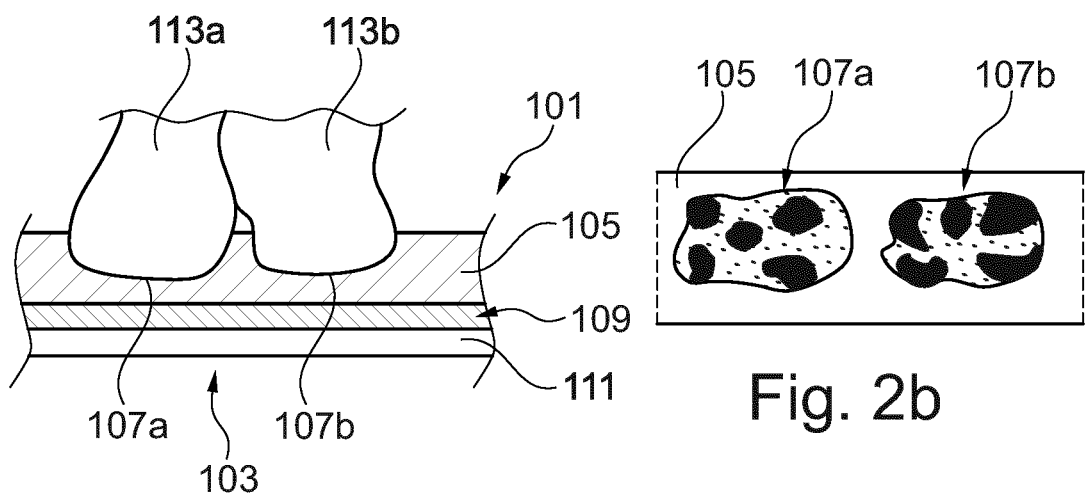
Fig. 2a
Fig. 2b

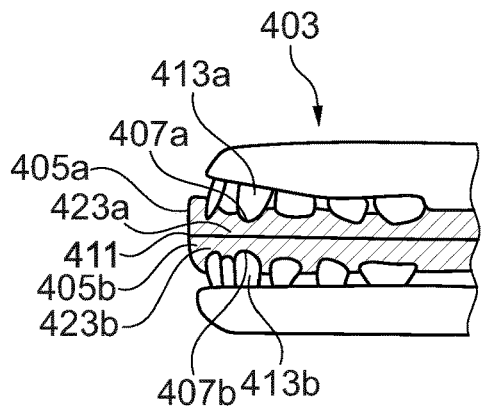
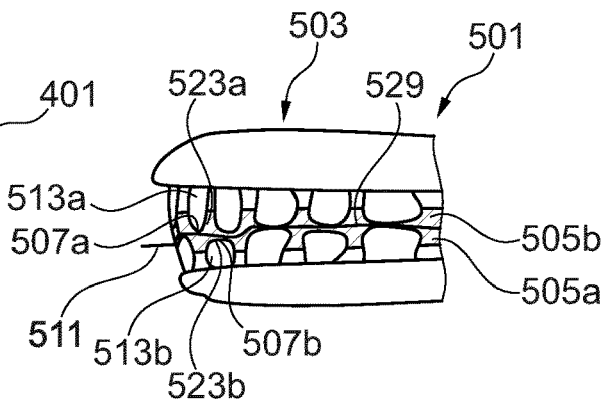
Fig. 5a    Fig. 5b
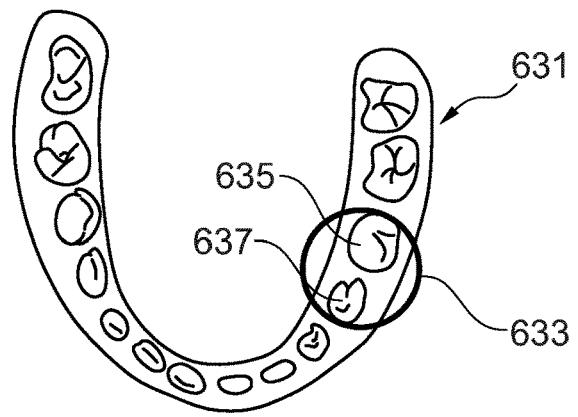
Fig. 6
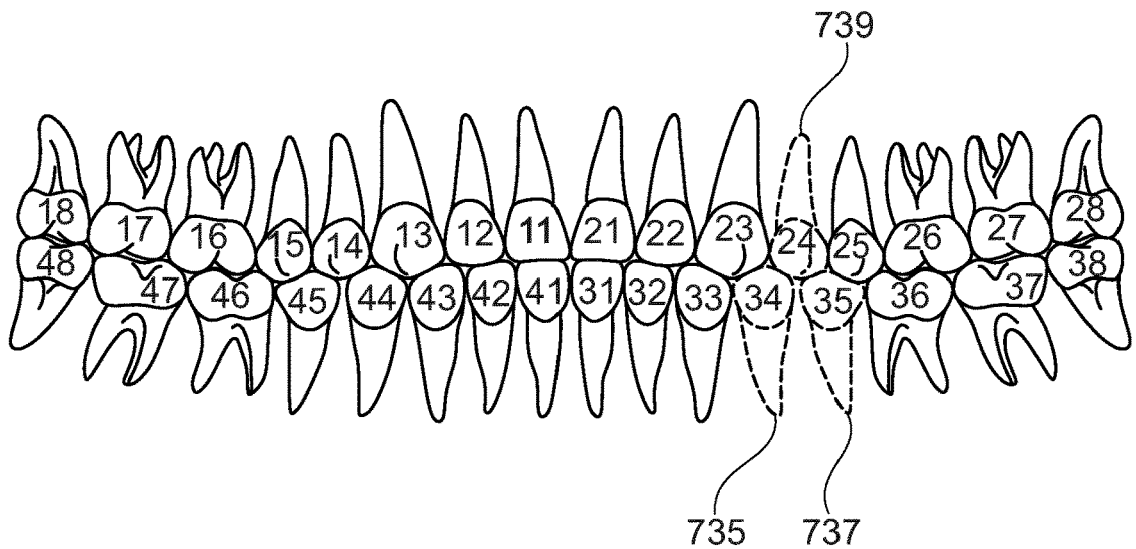
Fig. 7

INTRA-ORAL BITE DEVICE AND METHOD OF RECORDING AN ANATOMICAL FEATURE OF A PATIENT BY USING THE INTRA-ORAL BITE DEVICE

TECHNICAL FIELD OF THE INVENTION

The present invention relates to a bite device for use with an x-ray recording apparatus for recording the image of a dental area of a patient.

BACKGROUND ART OF THE INVENTION

When making x-ray image recordings of an oral/dental area of a patient, the fundamental problem arises that the recording angle and the recording area must be set such that x-ray exposure for a patient can be reduced. The recording area should be selected to be as small as possible for this purpose. On the other hand, the recording area should record all oral/dental elements such as the teeth, bones, jaws, soft parts of interest essential for the respective diagnosis. Furthermore, there is the problem that the image recording angle must be selected such that an overlap of different elements which can lead to unwanted coverages must be avoided. In general, a selection of the recording area is made by a trained personnel. Despite the relevant training, an imprecise selection of the recording area may occur. Frequently, the areas selected are too large in order to ensure that the relevant anatomy can be shown, and repeat recordings can be avoided to correct the recording area. Thus, an optimal setting of the recording parameters cannot generally be achieved by the trained personnel. In general, a positioning of a patient relative to the recording appliance has to date been achieved alternatively by means of a corresponding patient affixation such as a bite device. Through the bite device, the position of a patient can be approximately defined relative to the x-ray image recording appliance. See for example prior art documents EP1560520 and EP1793739. Further reference is made to US2015/0305669A and US2015/0327958A1 each disclosing a prior art bite device.

DISCLOSURE OF THE INVENTION

An objective of the present invention is to provide an intra-oral dental bite device and a method that enable the best possible alignment of the x-ray recording apparatus relative to the patient and an optimal selection of the recording area, and setting of the recording parameters.

These objectives have been achieved through the independent claims of the present invention. The dependent claims relate to further developments.

The bite device of the present invention has at least one sensor device, by means of which, at least partially, at least one feature of an anatomical structure of the patient is recordable in the bite area, and if desired also outside the bite area of the bite device. Here, the bite area at least partially comprises at least one deformable first material in operative connection with the sensor device, wherein by means of the sensor device, at least partially, the surface influenced by the dental element in the first material of the bite area is recordable for determining the anatomical structure.

According to the present invention the first material is either elastically or alternatively plastically deformable such that by means of at least one first sensor facility of the sensor device, the contour and surface of the anatomical structure of the patient, is recordable by means of at least partial sensing or alternatively scanning. The first material is at least partially, actively in contact with said sensor device, in particular with the first sensor facility. The sensing can be achieved through using piezoelectric, inductive, capacitive resistive, or pressure sensitive material and the like. The scanning of the anatomical structure of the patient, in particular inside and outside the bite area, can be alternatively achieved without contact, for example optically, acoustically or the like.

According to the present invention the bite device has at least one support structure, wherein the first material and the sensor device, in particular the first sensor facility thereof, are supported by the support structure. The sensor device, in particular the first sensor facility, is disposed at least partially between the first material and the support structure.

According to the present invention the bite device has at least one connecting element for connection of the bite device more specifically the bite area, the first material, the sensor device, the support structure with an x-ray recording apparatus, in particular with a support element of the x-ray recording apparatus. The connecting element comprises at least one joint, preferably at least one ball joint for moving the bite device relative to the recording apparatus, in particular to the support element. And the connecting element is actively connected with at least one third senor facility. By means of the third sensor facility, a relative position between the bite device and the x-ray recording apparatus, in particular the radiation source and the radiation detector of the recording device can be determined. The third sensor facility comprises at least one electro-optical or electro-magnetic tracking module or at least one inertial module and the like.

In general, the oral/dental element may comprise at least one oral cavity, at least one tooth, at least one occlusal area, at least one buccal area, at least one incisal area, at least one apical area, at least one cervical area, at least one upper jaw, at least one upper jaw arch, at least one lower jaw, at least one lower jaw arch or at least one gum. Therefore, according to the present invention the first material comprises at least one foam, at least one gel, at least one self-hardening material, at least one shape memory material, and/or at least one dental impression compound for effectively contacting the oral/dental element. Thereby, the contour and the surface of the anatomical structure is recordable at least in areas in the labial, lingual, palatinal, buccal, medial, distal, occlusal, incisal and/or cervical direction, in particular in relation to the oral/dental element. The sensor device, in particular the first sensor facility, is disposed at least partially in the labial, lingual, palatinal, buccal, mesial, distal, occlusal, incisal or cervical direction, in particular in relation to the oral/dental element and in operative connection with the first material.

According to the present invention, at least two deformable first materials may be disposed on the lower and upper sides of the bite area respectively to enable sensing of the shapes and positions of features of the anatomical structures relating to the oral elements on the upper jaw and lower jaw of the patient respectively. The support structure may have various shapes. Preferably, the support structure has an arch shaped upper channel and a lower channel each for accommodating a deformable first material and a first sensor facility.

According to the present invention, the support structure may optionally comprise at least a second material forming the support structure, wherein the second material may be either elastically or alternatively plastically deformable. The second material has preferably a lower degree of rigidity than the first material. The sensor device has a second sensor facility, wherein by means of the second sensor facility, the deformation of the support structure is recordable while the patient is biting down.

According to the present invention, the first and the second sensor facilities comprises at least one piezoelectric, inductive, capacitive or resistive, pressure sensitive material, at least one electro-optical, electro-acoustic, ultrasound, infrared sensor, or LED, laser and the like for sensing with or without direct contact.

According to the present invention, the x-ray recording apparatus comprises at least one x-ray source and at least one x-ray detector. The recording apparatus may be designed as an intra-oral x-ray apparatus or alternatively as an extra-oral x-ray apparatus. The recording apparatus may be designed as an x-ray volume tomography (DTV) recording apparatus.

The present invention also provides an x-ray recording apparatus having at least one radiation source and at least one radiation detector and at least one bite device according to the present. The bite device is at least partially disposable in the x-ray beam path from the radiation source to the radiation detector.

The present invention also provides a method for determining and recording at least one anatomical feature of a patient for controlling an x-ray recording apparatus for making a recording of an oral area of the patient. The method comprises the steps:
preparing a bite device according to the present invention; and
biting of the patient on the bite area with at least one oral element,
recording of at least one anatomical structure by means of the sensor device, wherein the anatomical feature is determined on the basis of the recorded anatomical structure.

According to the present invention, where the first material is plastically deformable, the contour and surface structure of the anatomical region can be recorded, for example after biting down and after removal of the bite device from the oral cavity of the patient, i.e. after the bite device has been plastically deformed by being bitten on. According to the present invention, where the first material is elastically deformable, the contour and the surface of the anatomical structure can be recorded during biting down when the bite device is elastically deformed.

According to the present invention at least one recording parameter, such as a sharp layer, at least the alignment of the recording apparatus, in particular of the radiation source and the radiation detector, the ray dose of the radiation source, the recording area of the recording apparatus, the irradiation angle of the recording apparatus, the trajectory of the recording apparatus, the aperture position of the recording apparatus or the radiation spectrum of the recording apparatus is determined on the basis of the sensed anatomical feature of interest, wherein the recording apparatus is controlled on the basis of the recording parameter.

According to the present invention the sensing of the contour and the surface of the anatomical structure may be also conducted at least at times while the x-ray recording is actively being made. And the recording parameter may be re-determined and adaptively altered, preferably continuously or at discrete times while the recording is being performed. According to the present invention the recording may be interrupted when the determined anatomical feature, in particular the contour and the surface of the anatomical structure lies outside a predetermined area.

According to the present invention, the x-ray recording is preferably a digital volume tomography (DVT) recording, in particular on the basis of the determined anatomical feature and the determined recording parameter, including a positioning and size of the volume associated with the determined anatomical feature, and the determined trajectory of the recording apparatus.

Herewith, the entire content of the priority application including the subj ect-matters of the description, the claims and the drawings are incorporated into this patent application by way of reference under the provisions of the patent cooperation treaty (PCT).

BRIEF DESCRIPTION OF THE DRAWINGS

In the subsequent description, further aspects and advantageous effects of the present invention will be described in more detail by using exemplary embodiments and by reference to the drawings, wherein FIG. 1 is a perspective upper view of a bite device according to the first embodiment of the present invention, which comprises a plastically deformable first material;

FIG. 2a is a schematic partial cross-sectional view of a bite device according to the second embodiment of the present invention during biting down of a patient;

FIG. 2b is a schematic illustration of the data recorded through the sensor device of the bite device of FIG. 2a;

FIG. 5a is a schematic partial side view of a bite device with a rigid support structure according to the fifth embodiment of the present invention;

FIG. 5b is a schematic partial side view of a bite device with an deformable support structure according to the sixth embodiment of the present invention;

FIG. 6 is a visualization based on the measurement data output by means of the bite device according to another embodiment of the present invention; and FIG. 7 is a visualization based on the measurement data output by means of the bite device according to an alternative embodiment of the present invention.

The reference numbers shown in the drawings denote the elements as listed below and will be referred to in the subsequent description of the embodiments.
1 Bite device
3 Bite area
5 Material
7a, 7b, 7c, 7d Impression
101 Bite device
103 Bite area
105 Material
107a, 107b Impression
109 Sensor facility
111 Support structure
113a, 113b Tooth
201 Bite device
203 Bite area
205 Material
209 Sensor facility
211 Support structure
215 Connecting element
217 Joint
219 Support element
221 Sensor facility 301 Bite device
303 Bite area
305a, 305b Material
307a, 307b Impression
309a, 309b Sensor facility
311 Support structure
313a, 313b Tooth
323a, 323b Occlusal area
325a, 325b Lingual area
327a, 327b Buccal area
401 Bite device
403 Bite area
405a, 405b Material
407a, 407b Impression
411 Support structure
413a, 413b Tooth
423a, 423b Occlusal area
501 Bite device
503 Bite area
505a, 505b Material
507a, 507b Impression
511 Support structure
513a, 513b Tooth
523a, 523b Occlusal area
529 Sensor facility
631 Bite piece
633 Selection area
635 Tooth
637 Tooth
735 Tooth
737 Tooth
739 Tooth FIG. 1 shows a schematic perspective view of a bite device 1 according to the first embodiment of the present invention. The bite device 1 has a bite area 3 established through a plastically deformable first material 5. In FIG. 1, the bite device 1 is shown in a state after a patient has bitten onto the bite area 3, and the bite device 1 has been removed from the mouth of the patient. Due to the plastic deformability of the first material 5, the impressions 7a, 7b, 7c, 7d of the oral elements can be clearly in seen in FIG. 1 having the form of the teeth which themselves have not been shown. Due to the fact that at the point in time at which the patient bites down, as will be further explained below, the bite device 1 was disposed in a predetermined position in space relative to the x-ray apparatus, and through sensing/scanning of the impressions 7a to 7d, a conclusion can be reached on the dental anatomy of the patient, in particular the position and shape of the teeth in space relative to the x-ray apparatus. The arrangement in FIG. 1 shows the bite device 1 for the upper jaw but may be duplicated to include the same elements also for the lower jaw. For this purpose, it is envisaged that the bite device 1 is subjected to a sensor device (not shown in FIG. 1) which analyses, in particular senses the anatomical structure influencing the bite area 3. The sensor device may be integral with or remote from the bite device 1. The position and shape of the teeth is then determined for example from the contour left on the bite device 1. On the basis of this data, the patient is then returned to the predetermined position, and on the basis of the sensed values, the recording parameters are set for making an x-ray recording. The x-ray recording parameters may include for instance a radiation dose and a recording area, in order to be able to view the oral area of the patient as required.

FIG. 2a shows a schematic partial sectional view of a bite device 101 according to the second embodiment the present invention. The reference numerals assigned to the bite device 101 correspond to those of the bite device 1 where increased by 100. In contrast to the bite device 1, in the bite device 101, the first material 105 used is elastically deformable. The first material 105 may be for example a foam material. The bite device 101 has a sandwich-type structure. A first sensor facility 109 of the sensor device is disposed below the first material 105. This first sensor facility 109 is in turn supported by a support structure 111. The arrangement in FIG. 2 shows only the bite device 101 for the upper jaw but may be duplicated to include the same sandwich-type structure also for the lower jaw. In the state shown in FIG. 2a, the patient bites down on the bite device 101 such that the oral elements leave impressions into the first material 105 having the form of the teeth 113a, 113b. Thereby, the impressions 107a and 107b are created in the first material 105. By means of the sensor facility 109 which is in operative contact with the first material 5, it is possible to record the deformation of the first material 105 and thus the contour and surface influenced in the bite area 103 can be sensed in a spatially resolved manner. FIG. 2b schematically shows in an example the measurement data that is delivered by the first sensor facility 109. On the basis of the measurement data, the scale to which the first material 105 has been compressed can be seen. The dark areas in the impression 107a or 107b shown in FIG. 2b, correspond to strong compression/deformations of the first material 105. Thereby, the chewing forces, and position and shape of the teeth 113a and 113b during biting down can be determined.

In alternative embodiments (not shown), the first material may be entirely or partially removed or provided at least partially transparently. And by means of the first sensor facility 109, the anatomical structure, such as the teeth 113a, 113b, can then be sensed/recorded without contact, for instance optically. Thus, the position and shape of the chewing surfaces and the like can be determined without contact, for instance through optical scanning.

Figure 3:
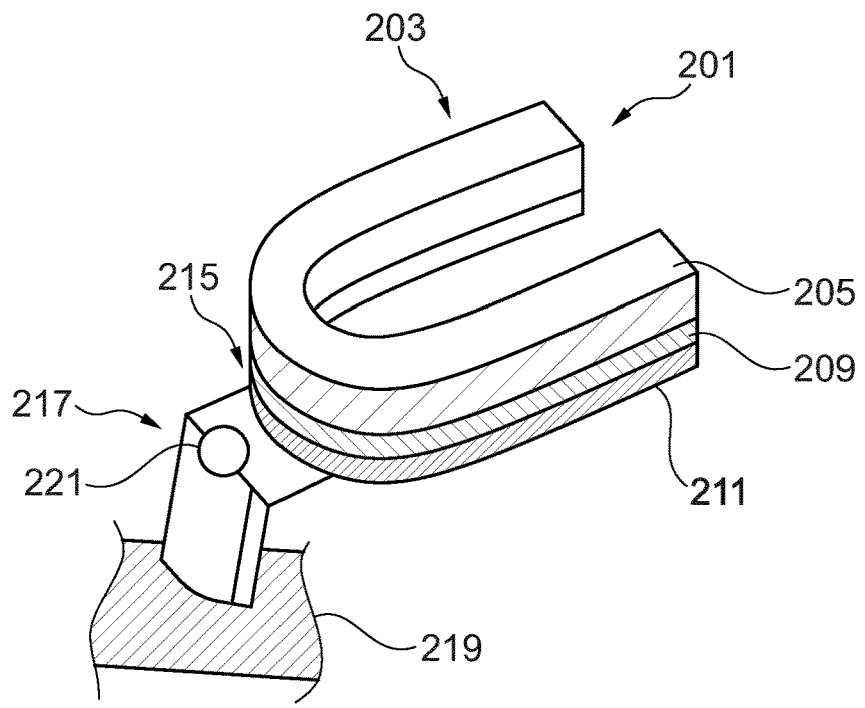
FIG. 3 is a perspective view of a bite device according to the third embodiment of the present invention.

FIG. 3 shows a schematic perspective view a bite device 201 according to the third embodiment of the invention. The elements of the bite device 201 that correspond to those of the bite device 101 bear the same reference numerals but increased through 100. The arrangement in FIG. 3 shows only the bite device 201 for the upper jaw but may be duplicated to include the same sandwich-type structure also for the lower jaw. The bite device 201 is designed such that when a patient bites down, the position and shape of the anatomical feature of at least the upper jaw of the patient can be sensed, output and recorded. For this purpose, the bite device 201 has a first material 205 in the bite area 203 below which a first sensor facility 209 is disposed. The sensor facility 209 and the first material 205 are supported by a support structure 211. The support structure 211 is connected via a connecting element 215, which comprises a joint 217 in the form of a ball joint, with a support element 219 of an x-ray recording apparatus. In order to record the position of the bite device 201 in space relative to the x-ray recording apparatus, the joint 217 has a third sensor facility 221. By means of the sensor facility 221, the position of the bite device 201, in particular of the bite area 203 in space can be determined. Hence by means of the data provided by the first sensor facility 209 and the second sensor facility 221, the geometry of the oral anatomical structure of the patient, when a patient bites down, can be determined relative to the x-ray apparatus.

Figure 4:
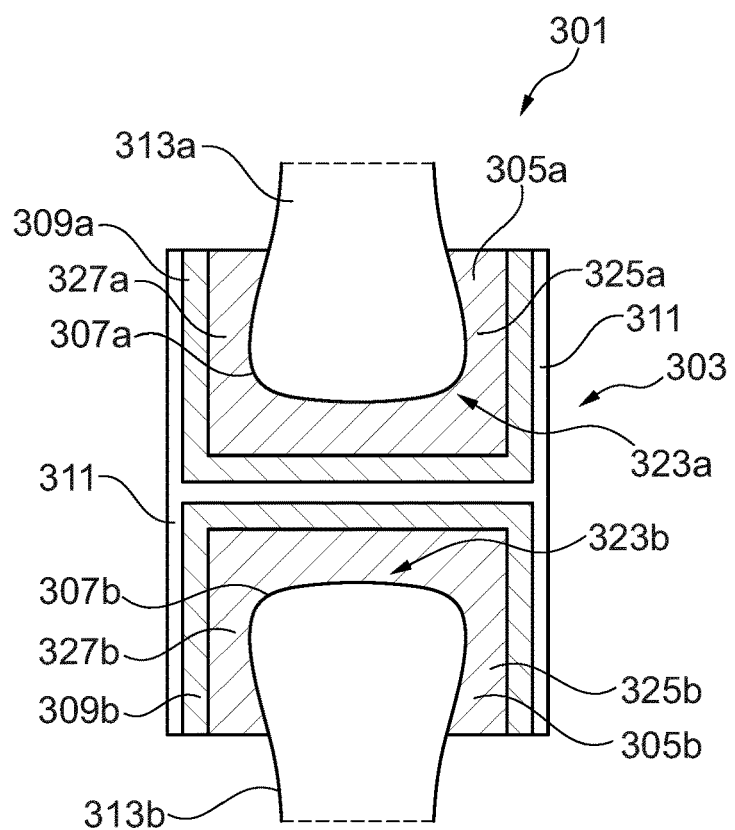
FIG. 4 is a schematic partial vertical cross-sectional view of a bite device according to the fourth embodiment of the present invention during biting down by a patient.

FIG. 4 shows a bite device 301 according to the fourth embodiment of the present invention. The elements for the bite device 301 that correspond to those of the bite device 201 bear the same reference numerals but increased by 100. The bite device 301 enables the simultaneous recording of the anatomical features of both a lower jaw and an upper jaw of a patient. For this purpose, the bite device 301 has first materials 305a and 305b on both sides of the bite area 303. The first materials 305a, 305b can be identical, but also different in their properties, specifically with regard to their rigidity and deformability. When the patient bites down on the bite device 301, an impression 307a is produced in the material 305a by the tooth 313a of the upper jaw of the patient, while an impression 307b is produced in the material 305b by the tooth 313b of the lower jaw of the patient. In order to record the position and shape of the teeth 313a and 313b, the first sensor facilities 309a and 309b record an occlusal area 323a and 323b, a lingual area 325a and 325b and a buccal area 327b and 327a. In other words, the sensor facility 309a and 309b can sense in the occlusal area and in the lingual area and in the buccal area of the teeth 313a and 313b. As a result, a precise determination of the position and shape of the tooth 313a and 313b is enabled, as a result of which a setting of the x-ray recording apparatus can be performed.

FIG. 5a shows a schematic partial sectional side view a bite device 401 according to the fifth embodiment of the present invention. The elements for the bite device 401 that correspond to those of the bite device 301 bear the same reference numerals but increased by 100. For the purpose of simplification of the drawing, the first sensor facility 109 has not been shown in FIG. 5a. As can be seen from FIG. 5a, the support structure 411 has a higher rigidity than the first material 405a and 405b, and which is not easily deformed when bitten on by the patient.

FIG. 5b shows a schematic partial sectional side view of a bite device 501 according to the sixth embodiment of the invention. The elements of the bite device 501 that correspond to those of the bite device 401 bear the same reference numerals but increased by 100. In the bite device 501, the support structure 511 is formed from a second material, which has a low rigidity than the first materials 505a or 505b, and is elastically deformable when bitten on by the patient. A second sensor facility 529 is integrated into the support structure 511, by means of which the deformation of the support structure 511 can be recorded. Thus, a precise determination of the position and shape of of the oral elements of the patient, in particular of the teeth 513a and 513b, becomes possible.

FIG. 6 shows a display of a bite piece 631 of a patient based on the output of the bite device 1, 101, 201, 301, 401, 50. By means of the bite device 1, 101, 201, 301, 401, 501 of the present invention, the precise radiographic imaging of the dental anatomy of the patient becomes possible. A user can now select a selection area 633 in the bite piece 631 of FIG. 6, and the x-ray recording can be carried out accordingly. In particular based on the position, size and alignment of the oral elements 635 and 637 with respect to the x-ray recording apparatus, the radiation dose, a recording angle etc. can be precisely determined such that the best possible recording of the oral elements 635, 637 is achieved.

Alternatively, the data recorded and output by means of the bite device 1, 101, 201, 301, 401, 501 can also be visualized in the manner shown in FIG. 7. Thus, a schematic view of the teeth of the patient, similar to a panoramic view is shown, and the user can select for example the teeth 735, 737 for the precise radiographic imaging. The advantage of the visualization in FIG. 7 is that the oral elements of the upper jaw, for example of the tooth 739, can also be shown and can be selected for a subsequent x-ray recording.

The invention claimed is:

1. A method of sensing an anatomical feature of a patient for controlling an x-ray recording apparatus for making an x-ray recording of an oral area of the patient, comprising:
providing an intra-oral bite device including:
an at least one bite area; a sensor device; one or more deformable first materials in operative connection with the sensor device and disposed on the at least one bite area; the intra-oral bite device is configured for use with the x-ray recording apparatus to record the oral area of the patient, the intra-oral bite device at least partially comes into contact with an oral element of the patient when bitten on; the sensor device is configured to record the anatomical feature of an anatomical structure of the patient in the at least one bite area;
responsive to a biting down on the at least one bite area with at least one oral element, sensing, the anatomical feature of the anatomical structure of the patient, and
controlling the x-ray recording apparatus through setting recording parameters on the basis of the anatomical feature, wherein the recording parameters include at least one of a sharp layer, orientation of the x-ray recording apparatus, radiation dose of the x-ray radiation source, recording area of the x-ray recording apparatus, an irradiation angle of the x-ray recording apparatus, a trajectory of the x-ray recording apparatus, an aperture position of the x-ray recording apparatus, and a radiation spectrum of the recording apparatus;
wherein the sensing of the anatomical feature is also conducted at times while the x-ray recording is being made and the recording parameters are concomitantly altered or maintained based on the anatomical feature, wherein the x-ray recording is interrupted when the anatomical feature lies outside a predetermined range.

2. The method according to claim 1, further comprising:
providing a display of the anatomical feature;
enabling the user to choose one or more teeth or a selection area enclosing one or more teeth in the display to be recorded by the x-ray apparatus,-setting the recording parameters of the x-ray apparatus according to the choice of the user and performing the x-ray recording.

3. The method according to claim 2, wherein the display comprises a panoramic view of the one or more teeth or a dental arch view of the one or more teeth.

4. An x-ray recording apparatus comprising at least one radiation source, at least one radiation detector, and a controller configured to:
provide an intra-oral bite device including:
an at least one bite area; a sensor device; one or more deformable first materials in operative connection with the sensor device and disposed on the at least one bite area; the intra-oral bite device is configured for use with the x-ray recording apparatus to record an oral area of the patient, the intra-oral bite device at least partially comes into contact with an oral element of the patient when bitten on; the sensor device is configured to record an anatomical feature of an anatomical structure of the patient in the at least one bite area;
responsive to a biting down on the at least one bite area with at least one oral element, sense, the anatomical feature of the anatomical structure of the patient, and
control the x-ray recording apparatus through setting recording parameters on the basis of the anatomical feature, wherein the recording parameters include at least one of a sharp layer, orientation of the x-ray recording apparatus, radiation dose of the x-ray radiation source, recording area of the x-ray recording apparatus, an irradiation angle of the x-ray recording apparatus, a trajectory of the x-ray recording apparatus, an aperture position of the x-ray recording apparatus, and a radiation spectrum of the x-ray recording apparatus;

wherein a sensing of the anatomical feature is also conducted at times while an x-ray recording of the oral area is being made and the recording parameters are concomitantly altered or maintained based on the anatomical feature, wherein the x-ray recording is interrupted when the anatomical feature lies outside a predetermined range.

* * * * *